Figure 1:
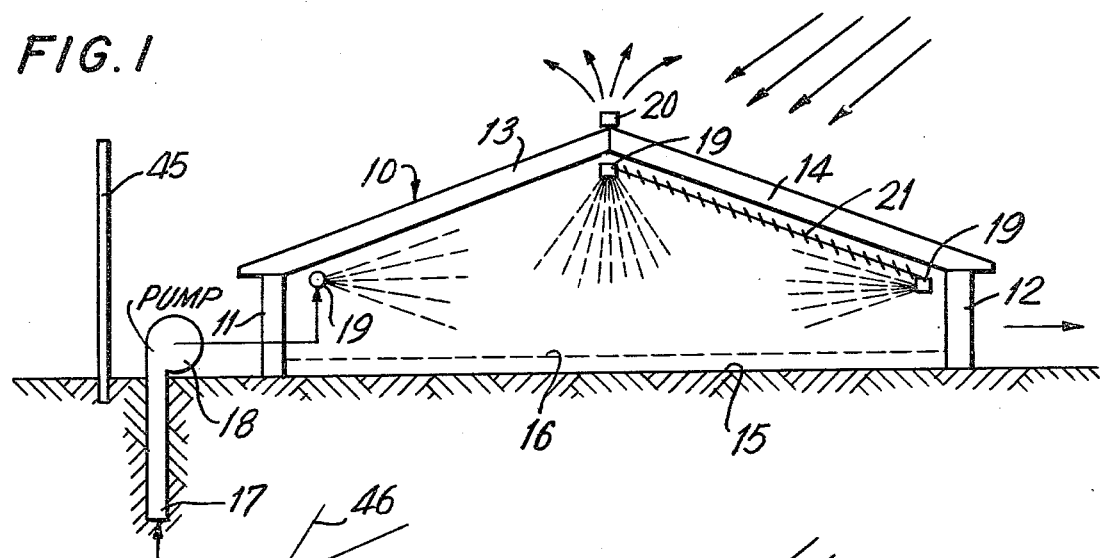

United States Patent [19]

Moeller et al.

[11] 4,209,943

[45] Jul. 1, 1980

[54] PROCESS AND APPARATUS FOR COMMERCIAL FARMING OF MARINE AND FRESHWATER HYDROPHYTES

[76] Inventors: Henry W. Moeller, 45 St. Andrews Rd., Southampton, N.Y. 11968; James P. Hunt, 200 Lexington Ave., Lyster Bay, N.Y. 11771

[21] Appl. No.: 830,163

[22] Filed: Sep. 2, 1977

[51] Int. Cl.² .................. A01G 31/02; A01G 9/18
[52] U.S. Cl. ............................ 47/1.4; 47/17; 47/58; 47/59; 47/65
[58] Field of Search .................. 47/1.4, 59–65, 47/17, 58; 165/45

[56] References Cited

U.S. PATENT DOCUMENTS

| | | | |
|---|---|---|---|
| 1,827,530 | 10/1931 | LeGrand | 47/17 X |
| 1,912,209 | 5/1933 | Lassen et al. | 47/17 |
| 2,620,335 | 12/1952 | Nielsen et al. | 47/1.4 X |
| 2,715,795 | 8/1955 | Pallotta et al. | 47/1.4 X |
| 2,732,661 | 1/1956 | Spoehr et al. | 47/1.4 X |
| 2,732,663 | 1/1956 | Dewey | 47/1.4 X |
| 2,807,912 | 10/1957 | Bjorksten | 47/58 |
| 2,854,792 | 10/1958 | Juda | 47/1.4 |
| 2,855,725 | 10/1958 | Carothers | 47/17 |
| 2,928,211 | 3/1960 | Martin | 47/60 |
| 3,016,801 | 1/1962 | Michel | 47/17 X |
| 3,195,271 | 7/1965 | Golueke et al. | 47/1.4 |
| 3,362,104 | 1/1968 | Oswald et al. | 47/1.4 |
| 3,403,471 | 10/1968 | Clement et al. | 47/1.4 |
| 3,529,379 | 9/1970 | Ware | 47/17 |
| 3,613,308 | 10/1971 | Klein et al. | 47/17 |
| 3,650,068 | 3/1972 | Meyer et al. | 47/1.4 |
| 3,653,150 | 4/1972 | Howard | 47/29 |
| 3,965,972 | 6/1976 | Peterson | 165/45 |
| 4,003,160 | 1/1977 | Muller | 47/1.4 X |
| 4,068,405 | 1/1978 | Campbell et al. | 47/65 |
| 4,073,089 | 2/1978 | Maginnes et al. | 47/17 |
| 4,095,369 | 6/1978 | Posnansky et al. | 47/17 X |
| 4,128,307 | 12/1978 | Badertscher et al. | 47/17 X |

FOREIGN PATENT DOCUMENTS

| | | | |
|---|---|---|---|
| 2304278 | 11/1976 | France | 47/17 |
| 34-9128 | 11/1959 | Japan | 47/1.4 |
| 45-940 | 1/1970 | Japan | 47/1.4 |
| 49-38596 | 10/1974 | Japan | 47/1.4 |
| 49-47836 | 12/1974 | Japan | 47/1.4 |

*Primary Examiner*—Robert E. Bagwill
*Attorney, Agent, or Firm*—Pennie & Edmonds

[57] ABSTRACT

The disclosure relates to the propagation and cultivation of freshwater and marine plants. These freshwater or marine plants are found naturally in underwater, floating or air-water interface habitats where sufficient illumination, nutrients and moisture are available to sustain life. A process is disclosed in which freshwater and marine macrophytes are cultivated in a water charged atmosphere, rather than in their native freshwater or marine environments, under precise control of such critical growing conditions as light, temperature, nutrient supply and disease control. Carbon dioxide, a plant nutrient is introduced into the atmosphere or into the water while other nutrients are provided through the use of controlled mists or sprays arranged to maintain a film of nutrient containing freshwater or seawater on the growing plants. Natural waters may be periodically enriched with organic or inorganic nutrients. Significant improvement in harvest efficiency is realized by water charged atmospheric culturing of the marine and freshwater macrophytes, such that harvesting of the hydrophytes on a commercial basis is feasible.

25 Claims, 8 Drawing Figures

PROCESS AND APPARATUS FOR COMMERCIAL FARMING OF MARINE AND FRESHWATER HYDROPHYTES

BACKGROUND AND SUMMARY OF THE INVENTION

Freshwater and marine plants represent important potential sources of food and chemicals. For example in the Orient, macroalgae are consumed extensively as a human food source while in many areas of the world they are used for animal feeds, medicine, animal feed supplements and fertilizers. In the United States, macroalgae are presently used for the production of agar, algin, and carrageenin. Current demand for these useful marine and freshwater macrophytes greatly exceeds their availability, at least on an economical basis. A basic objective of the invention, therefore, is to provide procedures and means for the large scale commercial culture, on an economically feasible basis, of fresh and salt water macrophytes.

Marine and freshwater macrophytes with which the invention may be employed include macro forms in the Subkingdom I Prokaryonta Division Cyanochloronta, Subkingdom II. Chloronta, Division Chlorophycophyta (green algae), Phaeophycophyta (brown algae), Chrysophycophyta Xanthophyceae (yellow green algae), Rhodophycophyta (red algae), Charophyta (stoneworts). Hydrophytic members of Hepatophyta (liverworts), Bryophyta (mosses), Pterophyta (ferns) and Anthophyta (flowering plants) are also included in this invention.

There is one fundamental underlying difference in cultivation technique among hydrophytic members of the various plant classification groups presented above. A number of plants derive nutrition from the water i.e. *Chondrus crispus* (Rhodophycophyta), *Riccia natans* (Hepatophyta), *Azolla* (Pterophyta) and *Lemna* (Anthophyta). Other plants derive mineral nutrition from the bottom sediments via anchored rhizomes or roots i.e. Watercress (Anthophyta). Intergradations between the two physiological extremes are also known. This invention may be employed for hydrophytes which derive their nutrition from the water or bottom sediments or some intergradation in between.

*Chondrus crispus* and *Gigartina stellata* are a source of carrageenin for commercial applications and are of particular interest in this invention. If not found floating in their natural habitat they are found attached to a substrate not by a root system but by a holdfast. Nutrients are not obtained from the bottom sediments but from the surrounding water. Often due to water movement caused by tidal currents, wave action and other forces, these plants are in constant motion which provides maximal exposure to sunlight as well as water bearing nutrients.

We have found that both *Chondrus crispus* and *Gigartina stellata* grow faster in water charged atmosphere than underwater under equivalent conditions and grow without attachment as well as obtain nutrients from the surrounding spray or mist.

In accordance with the present invention, freshwater and marine macrophytes are grown in a controlled, substantially closed atmosphere, in which the plants may be continually wetted by a mist or spray or the nutrient-containing water, either fresh or marine, as the case may be. This technique enables optimal conditions of light, temperature and nutrition utilization to be maintained, resulting in greatly enhanced growth rates and harvest cycles as compared to conventional underwater techniques for culturing and harvesting. When freshwater or marine hydrophytes are removed from their native aqueous habitat and furnished a quantity of water-borne nutrients by means of a spray or mist it results in the formation of a thin film of liquid on the plant foliage. The thin film culture technique results in a significant improvement of nutrient utilization and growth rates are greatly enhanced. By comparison, prior efforts to stimulate the growth of macroalgae in their natural environment have proven to be of limited effectiveness, for several reasons: among them, efficient use of nutrient additives is almost impossible to achieve in open water because of the necessity of dispersing sufficient quantities of costly fertilizer into a rather large volume of water, which typically may be subject to at least some degree of current flow which carries the nutrients away from the intended targets. In addition, significant amounts of the fertilizer may be taken up by weed species as well as the cultivated plants, often with undesirable results.

Pursuant to one of the more specific aspects of the invention, nutrient additions may be controllably imparted to the sprayed freshwater or seawater vehicle, not only to enhance growth rates but also to control the desirable product ratio of the plants. In addition to achieving greater nutrient efficiency, one may controllably impart to the sprayed freshwater or seawater vehicle plant growth substances, hormones, antibiotics, fungicides and herbicides. After harvest, shelter sterilizing agents may be introduced prior to restocking the cultivar.

The sun is man's primary source of energy and the amount of energy which reaches the earth's surface is colossal. Unfortunately, when light penetrates water it is subject to the exceptional light absorbing qualities of the water. Even in transparent water free of wave action significant amounts of sunlight are absorbed in the upper layers of water, making limited light available for photosynthesis, particularly when solar energy is relatively low due to variational solar radiation with the seasons and variable cloud cover. Thus, the average efficiency with which plants convert solar energy is low and as a result plants store something like 0.1 to 0.2% of available radiation annually. Plants like the water hyacinth on the other hand may have a very high conversion efficiency given sufficient radiation. In the process of the present invention, cultivation of marine and freshwater hydrophytes in the atmosphere, supplemented by a fine mist or spray, enable greater efficiencies to be realized in the trapping of solar energy, since less solar radiation absorption occurs. Thus, plants grown in the atmosphere in a spray or mist environment will receive more solar energy on a daily as well as seasonal basis.

In general, the apparatus of the invention includes a transparent solar shelter, forming a substantially enclosed atmospheric environment having large roof areas exposed on an axis suitable for achieving maximal solar radiation. Provisions may be made for minimizing the effectiveness of the sunlight during times of intense light, and for enhancing the sun's rays at low angles. Pursuant to the invention, provisions are made inside the transparent solar shelter for maintaining a rather constant fog or mist of freshwater or seawater, supplemented by periodic additions of nutrients and growth substances. For the group of hydrophytes which require rooting in the sediments, the plants are cultivated on the floor of the shelter in either a sediment or hydroponic culture. For the group of plants which obtain nutrition from the water, appropriate racks are provided for holding those plants during the growth cycle and, if desired, the racks may be in the nature of rotatable cylinders or the like.

The use of a spray medium for mariculture has four significant advantages over present aquacultural practices employing water in pools or underwater farming techniques. The most practical advantage is that less water is required (e.g., a cubic foot of seawater, weighs approximately 1000 oz. while a cubic foot of air at 100% relative humidity, 55° F. and one atmospheric pressure contains 0.01 oz. of water vapor). Therefore under theoretical conditions five orders of magnitude less water is required resulting in a significant reduction in cost of heating and cooling. A process employing a water charged atmosphere also allows for more uniform distribution of nutrients to the plants because the control of nutrients in the much smaller quantity of water, is far greater and significant economic benefits are thus realized. Further, since the volume of water employed is minimal in comparison to existing methods, it is economically feasible to utilize filtration techniques, e.g., ultraviolet sterilization and filtration for bacteria, fungi, phytoplankton and zooplankton, control of pathogens or symbionts, etc.

A further advantage of the use of a spray medium is that the particle size of the spray can vary from micron size to raindrop size, and spray nozzles are readily available for this broad range. The new method can make use of several particle sizes, depending on the desired effect. For example, a fine mist can be used for more effective nutrient distribution, and large droplets can be used to "wash" the plants for disease control or when they accumulate particulate matter or extracellular metabolites or organisms lightly attached or clinging to the cultivar. Moreover, if water mist is introduced at temperature A into an air atmosphere at temperature B then the heating/cooling efficiency is a function of heat transfer surface area. Therefore, the fine mist particle size is more efficient than the large particle size in heating and cooling the water charged atmosphere for equivalent masses of water.

For a more complete understanding of the above and other features and advantages of the invention, reference should be made to the following detailed description of preferred embodiments and to the accompanying drawings.

DESCRIPTION OF THE DRAWINGS

FIG. 1 is a simplified schematic illustration of one preferred form of controlled environment, transparent solar shelter according to the invention, for use in carrying out the procedures of the invention.

FIG. 2 is a schematic view of a modified form of transparent solar shelter for carrying out the processes of the invention.

FIG. 3 is a highly simplified, schematic diagram illustrating a typical piping system for utilization in the controlled environment shelter arrangements of FIGS. 1 and 2.

FIG. 4 is a simplified representation of yet another form of controlled environment transparent solar shelter utilizing rotary, cylindrical racks for holding plants not requiring roots in the sediments during the growth cycle.

FIGS. 5 and 6 are simplified views illustrating further details of the rotary cylindrical racks utilized in the arrangement of FIG. 4.

FIG. 7 is a simplified perspective illustration of an advantageous form of cellular roof panel, for utilization in the controlled environment shelters according to the invention.

FIG. 8 is an enlarged cross sectional detail as taken generally along lines 8—8 of FIG. 7.

DESCRIPTION OF PREFERRED EMBODIMENTS OF THE INVENTION

In the process of the invention, hydrophytes of the general classes heretofore referred to are cultivated in the water charged atmosphere, in an enclosed environment, rather than in their natural aqueous environment. With reference to FIG. 1, for example, a transparent shelter structure 10 may be formed of transparent or translucent materials, including side walls 11, 12 and a peaked roof structure comprising roof panels 13, 14. The orientation of the enclosing structure 10 desirably is such that the roof panels 13 are arranged on an axis suitable for achieving maximal solar radiation.

In the illustrated arrangement, the enclosure 10 is formed with a base or grade layer 15 of stone aggregate, which provides efficient drainage. Spaced above the stone aggregate base is a rack structure 16. The specific structure of the rack is not a part of the present invention, although it is a nontoxic, open mesh-like structure which serves to support the propagates or cultivars above the grade layer, while providing for the relatively free circulation of air in and about the plants and for the drainage of excess liquid through to the aggregate base 15. For rooted plants, the aggregate bed and rack structure may be replaced by suitable sediments, and mesh may be used to support and orient the plants in the atmosphere.

Within the enclosing structure 10 there are provided a plurality of spray heads 19, arranged to discharge a fine spray or mist of the nutrient vehicle, which is typically freshwater or seawater, depending upon whether freshwater or marine plants are being cultivated. The nutrient vehicle, as will be discussed further, may be used in its as-received condition, or may be selectively fortified by the addition of nutrients. In the particular arrangement shown in FIG. 1, the nutrient vehicle is derived from an adjacent well 17 or submersible pump in a water body extending to an appropriate source of freshwater or seawater. This water is directed by a pump 18 to the various spray nozzles 19 located appropriately throughout the enclosure so as to enable the entire plant growth to be periodically maintained with a wet film of the nutrient vehicle. Drying periods may be desirable for disease control.

Since maintenance of uniform temperatures is significant to efficient cultivation, provision is made in the process of the invention for maintaining the atmosphere within the enclosure 10 substantially in a desired or optimal range for the specific hydrophyte under cultivation. We have found in our experiments with Irish Moss that the optimal temperature range is from 10° to 21° C. at Montauk, New York. In warmer climates and seasons, it is particularly important to prevent water charged atmospheric temperature from changing quickly about a uniform optimum. A uniform temperature may be accomplished by utilizing water extracted from a deep well, as well water typically is extracted year around at a uniform temperature, without any significant seasonal variation. When well water is insufficient, additional cooling means are provided. In the arrangement illustrated in FIG. 1, an external spray means 20 is provided, which sprays water on the external surfaces of the roof panels 13, 14 for evaporative cooling. Other appropriate means may also, of course, be utilized for optimizing temperature.

Inasmuch as excessively intense sunlight can inhibit growth of some hydrophytes under propagation or cultivation, means may be provided for reducing the intensity of light at certain times. For this purpose, a roof panel 13 may be provided interiorly or exteriorly with 3M light control film or movable baffles 21 which may be controllably positioned for reducing light intensity. Such baffles may also be utilized for heat control in some instances, as by providing the rotatably mounted baffles with highly reflective surfaces on one side, light-absorbing surfaces on the opposite side.

Figure 3:
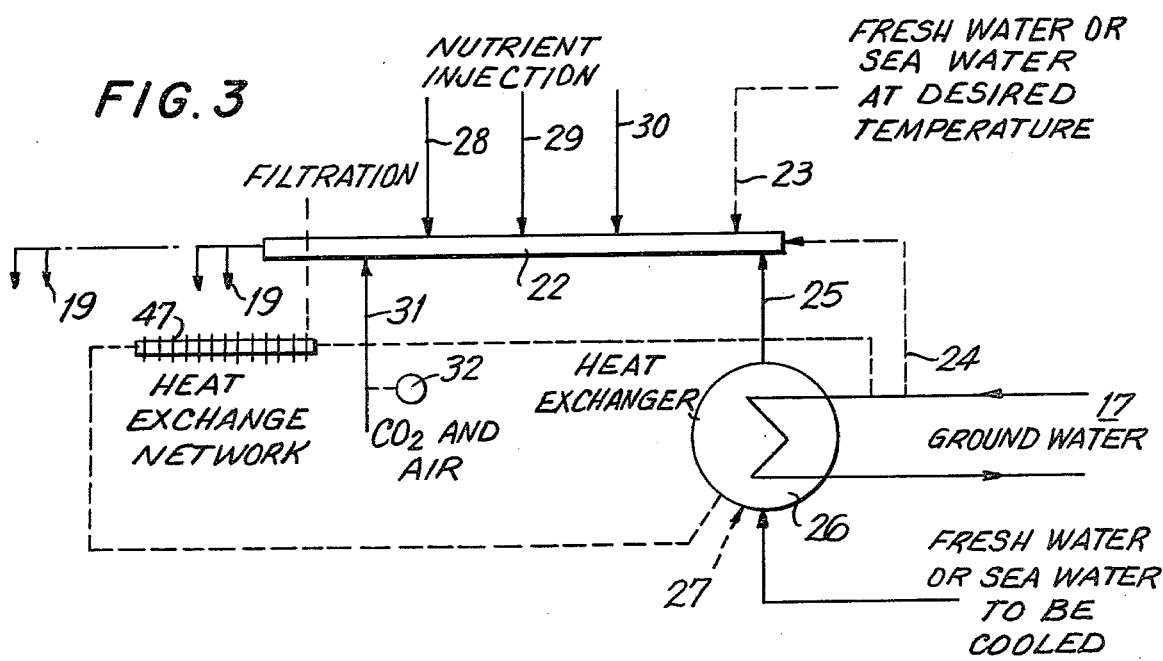

With reference to FIG. 3, a suitable distribution manifold 22 is provided, which leads to a plurality of spray discharge nozzles 19. The primary input to the distribution manifold 22 may be one of several incoming lines 23, 24, 25, depending upon the circumstances of location, season and the cultivar employed. For example, where seawater is available at the desired temperature levels, it may be introduced directly into the manifold 22 through the inlet line 23. Where seawater is available, but at a higher temperature than desired, it may be passed first through a heat exchanger 26 and then through an inlet line 25 into the distribution manifold. The heat exchanger 26 may be supplied with heat exchange medium in the form of ground water from the well 17. Where the ground water itself is to form the desired nutrient vehicle, it may be introduced directly into the distribution manifold 22 through the inlet line 24. In some cases, it may also be possible to use industrial waste water or sewage effluents for nutrient enhancement. Typically, these would be filtered and then introduced through an inlet line 27, passing through the heat exchanger 26 and then into the distribution manifold.

In the distribution manifold, provisions are made as at 28–30, for the introduction of desired organic and inorganic nutrients, as at 31. In the process of the invention, as carried out in an installation reflected in FIGS. 1 and 3, non-rooted plants to be cultivated are established on the rack 16, supported in the water charged atmosphere within the enclosed structure 10. A nutrient vehicle is furnished to the growing plant by means of the spray nozzle 19, periodically activated to maintain a film of liquid on the plant surfaces, while maintaining the relative humidity within the enclosure substantially at 100% (although it may be desirable on occasion to permit the plants to dry out for desease control purposes).

During the daylight hours, the amount of sunlight reaching the plants advantageously is controlled as necessary, primarily to prevent or minimize excessive light intensity, which has been found to be inhibiting to growth, and also to maximize the light during periods of minimum intensity. Likewise, external cooling is provided, if necessary, to avoid exposure of the plants to temperature significantly in excess of their optimal ranges.

Desired nutrients, such as nitrogen and phosphates, for example, are added into the nutrient vehicle, at the distribution manifold 22, shortly before the water is discharged from the spray nozzles 19. Several highly significant advantages are achieved from this method of nutrient application. First, as compared to adding nutrients to a natural aqueous environment, the amounts required are less by orders of magnitude, such that nutrient additions in accordance with the process of the invention are economically realistic. Secondly, the nutrients are applied directly to the hydrophyte, so that the value of the nutrients is substantially realized. When seeking to add nutrients to the natural aqueous environment, it is often difficult to maintain the nutrients in the water in the vicinity of the cultivar for an adequate period of time to enable the hydrophytes to obtain significant benefit. In addition, in the process of the invention, the plant supporting rack structure 16 contains substantially only the harvestable plant, whereas the natural environment includes significant amounts of undesired "weeds". When adding nutrient to a natural body of water, the weeds as well as the desired, harvestable plants are being fertilized, often with undesirable results.

It is known that plant growth can be significantly encouraged by enrichment of the atmosphere with $CO_2$. For this purpose, the invention contemplates controlled additions of $CO_2$ into the atmosphere or water. Ideally, gaseous $CO_2$ is discharged directly into the atmosphere within the enclosing structure 10, through gas nozzles (not specifically shown). In addition, nozzles 19 may be of an air-atomizing, liquid discharge type (conventional) such that the uniform discharge of the gaseous medium assists in atomizing the liquid nutrient medium, forming a finer mist or spray. Typically, the volume of gas required for this purpose may be substantially greater than the necessary requirements of $CO_2$, in which case the gaseous discharge may constitute the desired amount of $CO_2$ diluted with ordinary air. Further, since $CO_2$ is a reactant required for photosynthetic activity, it may be desirable to control the introduction of the $CO_2$ gas by means of a valve 32 which is responsive to the level of light within the enclosure. The valve 32 can be set to terminate the flow of $CO_2$ (but not necessarily the atomizing air itself, if utilized) when the level of light is too low for efficient photosynthesis. In general, when $CO_2$ enrichment is employed, it is controlled to achieve a concentration of around 100–1500 ppm of $CO_2$ in the controlled atmospheric environment.

Figure 2:
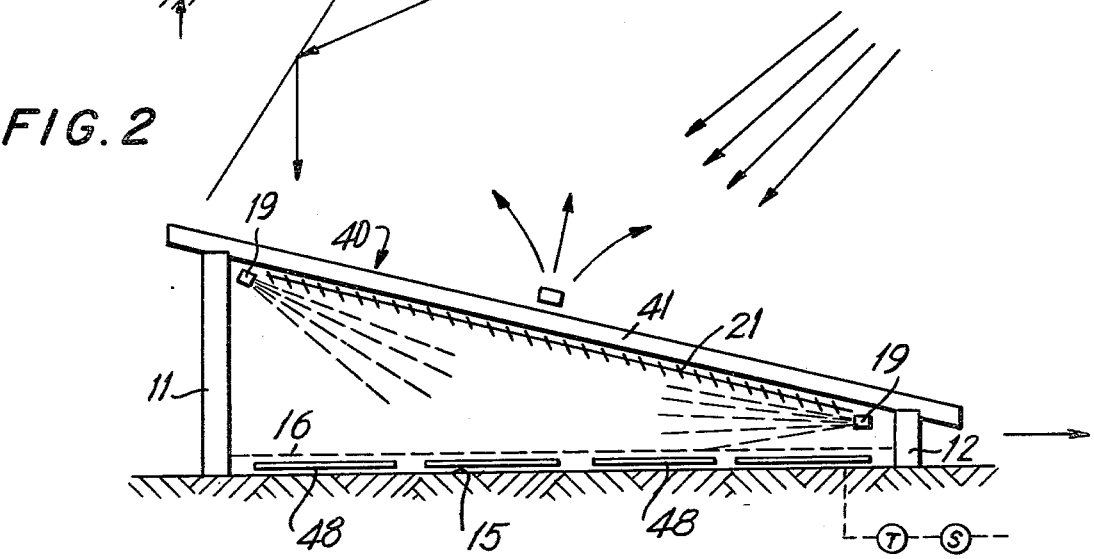

In the structure 40 illustrated in FIG. 2, the entire roof panel 41 faces on an axis suitable for achieving maximal solar radiation. In other respects, the structure of FIG. 2 may correspond to that of FIG. 1. When appropriate, similar reference numerals are employed to designate corresponding parts.

In any of the various forms of enclosing structure, auxiliary structures may be provided for controlling sunlight and/or temperature conditions. Thus, in the illustration of FIG. 1, a wind screen 45 may be provided along one or more sides of the structure, for minimizing convective heat loss in the cold seasons. Likewise, as reflected in the arrangement of FIG. 2, a light-reflecting structure 46 may be provided for enhancement of sunlight in the colder seasons. The reflecting structure, if desired, be adjustable to enable it to be oriented in an optimum position with respect to the height of the sun at a given time. Additionally, any of the various structures may utilize direct heat exchange means for controlling the temperature within the structure. One such arrangement may include the provision of an appropriate heat exchange network 47 (FIG. 3), which may be made up of finned tubing, for example, and which can carry either heating or cooling medium as the case may be. To advantage, such a heat exchange network may be furnished with ground water from the well 17, to provide both cooling in the warmer seasons and heating in the colder seasons, as desired.

In some temperate and southerly climates, the amount of available sunlight during at least some seasons is far greater in intensity than is either necessary or desirable for optimum cultivation of the freshwater and marine hydrophytes contemplated by the invention. Accordingly, provisions may be made, as reflected in FIGS. 4–6, for movably supporting the plants, enabling them to be successively and periodically brought into position to receive sunlight, and then returned to a more shaded location. Where adequate sunlight is available for this purpose, it is possible to increase the density of plant growth within a structure of given size, to improve the overall economics of the process.

In some cases, supplemental light may be desired to increase the growth cycle in periods of low natural light, and/or where control over day length and photo period is desired. With reference to FIG. 2, artificial lights 48 are located under the rack 16 (or at any other desired location). Such lights may be controlled by a timer T and light sensor S connected in series, whereby if the light level is below threshold during the light cycle period, the natural light is augmented by the lamps 48.

Figure 4:
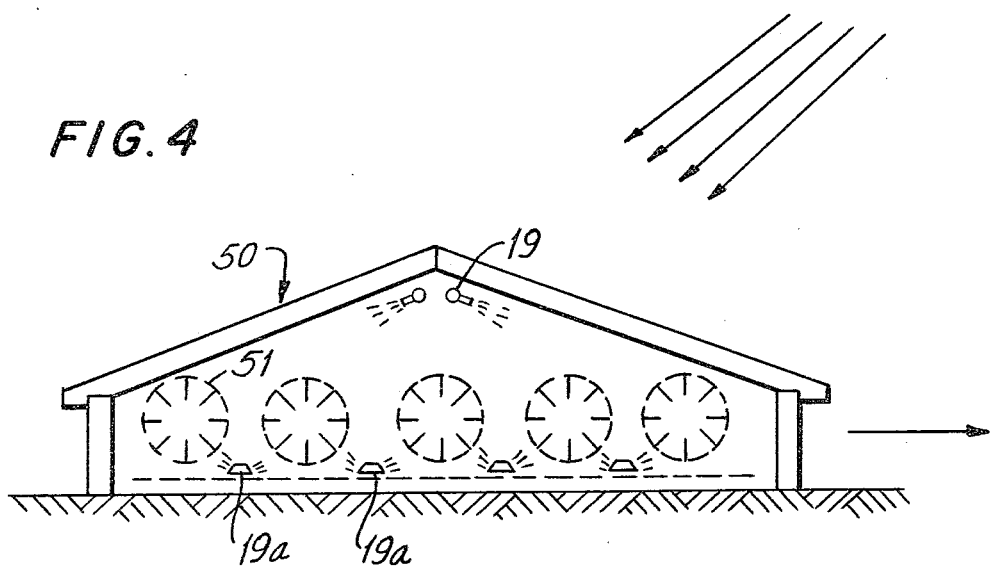
Figure 5:
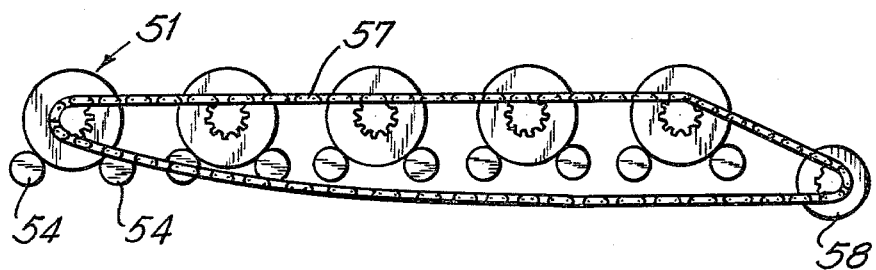
Figure 6:
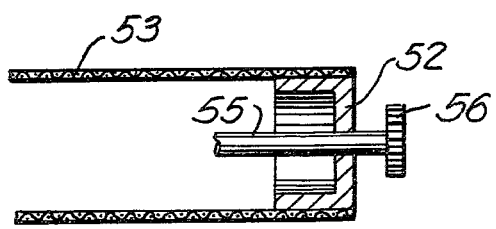

With specific reference to FIGS. 4–6, a structure 50 is illustrated, which can be constructed along the lines indicated in FIGS. 1 or 2. Within the structure, there are a series of plant-supporting racks 51, which are generally cylindrical in nature and are mounted for rotation about their respective axis. By way of example only, the cylindrical racks or drums may include end support frames 52 at each end, between which extend cylindrical sections 53 of nontoxic mesh or netting 53, which provide an open structure for the support and attachment of the plants. Pairs of rollers 54 at each end rotatably support the end frames 52. Each of the rotary assemblies is keyed to a shaft 55 which carries a sprocket 56 at its end engaging a common drive chain 57. The chain 57 is driven by a suitable motor drive arrangement 58, which is speed-adjustable to enable the racks to be rotated at a controlled speed appropriate for the level of sunlight. In the structure of FIG. 4, additional spray heads 19a may be mounted underneath the racks 51, directed upwardly. These spray heads may be pulsed on a periodic basis during the photocycle period to facilitate periodic reorientation of the plants to the light source.

The rotary rack arrangements reflected in FIGS. 4–6 may tumble the unattached plants to facilitate periodic rotation of the plants to the light source thus enabling the growth density to be increased within a structure of given size. The racks also facilitate periodic harvesting of mature plants from the racks since the harvest may be removed in "containerized" units.

Figure 7:
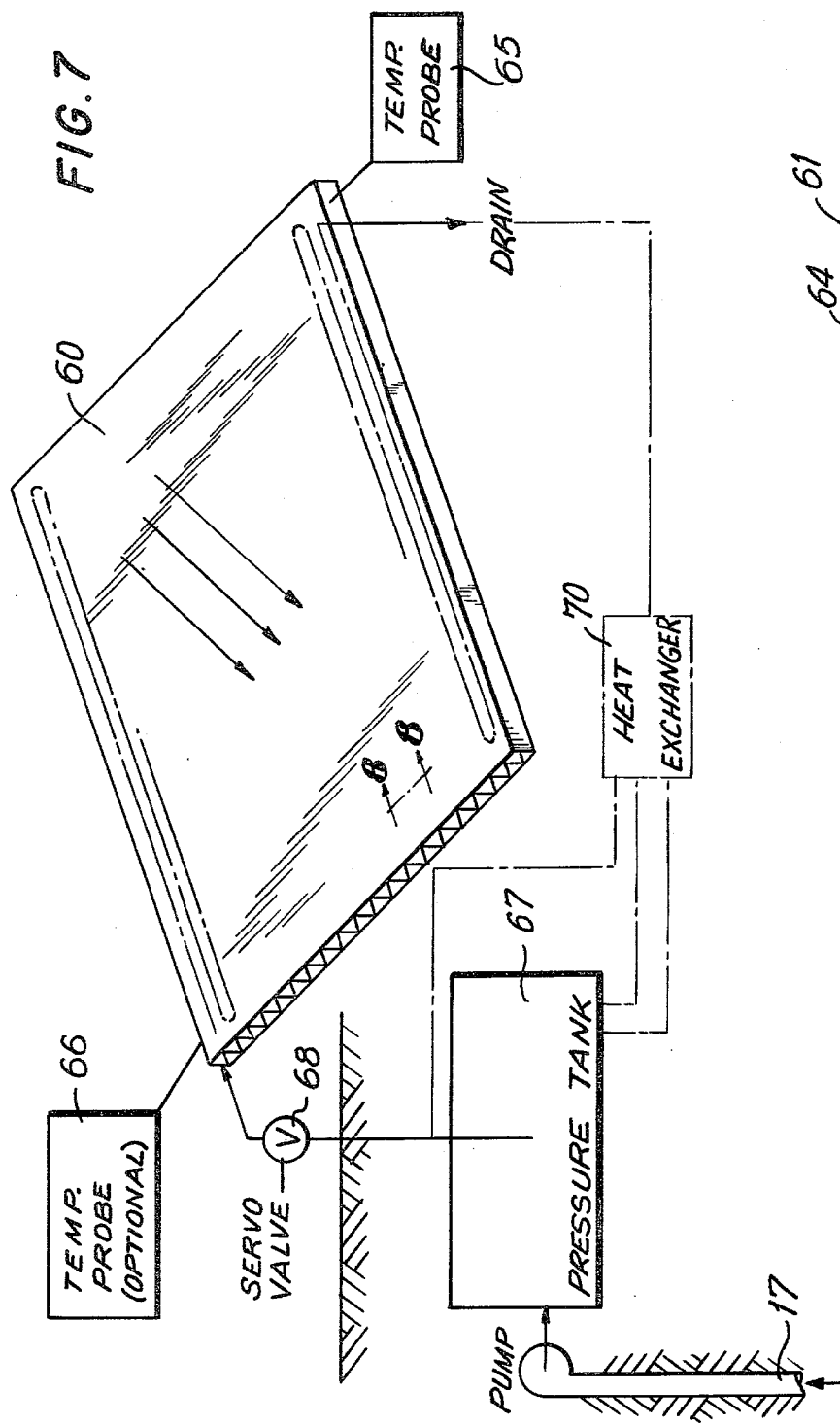
Figure 8:
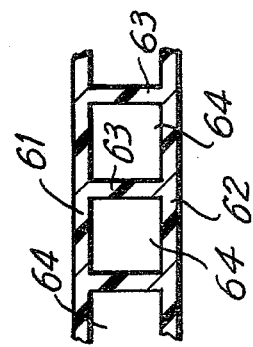

In FIGS. 7–8, there is illustrated a particularly advantageous arrangement for controlling temperature within a transparent solar shelter utilized in the process of the invention. Thus, in FIG. 7, the reference numeral 60 designates generally a panel unit utilized in forming a roof panel of the enclosing structures 10, 40 of FIGS. 1 and 2. The panel 60 advantageously is of a double skinned, ribbed construction, having an outer wall 61 (FIG. 8), in inner wall 62, and a series of relatively closely spaced ribs 63 extending between and supporting the inner and outer walls in the desired spaced relation. Adjacent pairs of the ribs 63 also form extended, longitudinal channels through the panel, and these are, in accordance with the invention, connected at the end of the panel, such that adjacent longitudinal channels 64 are connected in series. A suitable commercially available material for this purpose is Cyro double skinned acrylic panel, sold under the trade designation Acrylic SDP. The material of the panel is, in accordance with the invention, formulated to absorb a percentage of the infra red energy of the sunlight. In doing so, a portion of the heat energy of the sunlight is converted to heating of the roof panel 60. The panel itself is then cooled by directing through the series-connected channels 64 a flow of cooling medium, advantageously water taken from the underground well 17. To advantage, the flow of cooling medium through the roof panel 60 may be controlled by one or more temperature probes 65, 66, which regulate water flow from a pressure tank 67, by means of a servo valve 68.

For operation in the cold seasons, when low outside temperatures prevail, rather than excessive light and heat, the roof panel 60 may be emptied of the heat exchange medium during the daylight hours, for maximum transmission of sunlight, and then filled with the flowing medium during the dark hours, to serve as a heating medium at those times.

In many instances, it may be desirable and advantageous to provide for the circulation of cooling or heating medium through the series-connected channels of the roof panel 60 in a closed loop system, including a groundwater heat exchanger 70. When utilizing a closed loop system, the cooling or heating medium may include appropriate additives, such as light-absorbing chemicals, algacides or dyes, for reduction of light intensity and/or selective absorption of undesirable wavelengths. When using the closed loop system, the groundwater serves only in a heat exchange function and does not itself enter the panel 60.

We have observed plastic pipes, fiberglass, plastic netting and various types of rope can be used as an effective substrate for cultivating macroalgae propagates provided the substrate is properly cleaned of oil, grease and dirt. It is necessary with nylon rope to expose it for extended periods of time in the water and then to repeatedly autoclave it. Once the substrate has been prepared for our application we insert the substrate as a core inside an expandable netting. We have found DuPont material "Vexar" ideal for this application. Mature reproductive macroalgae are then loosely packed in the netting around the core substrate and placed in a conducive environment for growth. After the propagates become established and attached on the substrate core we remove the adult plants and expandable surrounding netting and then place the substrate core with the propagates in the transparent solar shelter or the natural environment where they are cultivated under the previously described growth regimen.

a polysaccharide complex known as carrageenin is a widely used hydrocolloid, which is now commercially derived from Irish moss and other macroalgae. It is used as a food additive, for example, and also has wide industrial uses. In accordance with one aspect of the invention, the growth cycle of the plants may be so controlled as to enhance the relative proportion of carrageenin in the harvested product. Thus, while plant growth is greatly encouraged by nitrogen enrichment of the nutrient medium, carrageenin levels in the plant are relatively low during this active growth period. However, after the plant has achieved a desired growth stage, the aqueous nutrient medium supplied to the plant by the spray nozzles 19 is caused to be relatively depleted of nitrogen content, resulting in a significant increase in the relative proportion of carrageenin in the plant. By way of example, carrageenin content has been known to increase by as much as a third when the plant is transferred from a nitrogen rich medium to a nitrogen depleted medium.

An important advantage of the present invention results from the ability to minimize effects of extracellular excretions by hydrophytes. In nature, a variety of extracellular products, derived from photo assimilated carbon, are excreted into the aquatic environment. While these substances are not fully understood, it is known that at least some of them tend to inhibit the growth of the plant. In the process of the present invention, the effects of such extracellular products are minimized. Moreover, the production of such products may also be reduced by proper control of the growing environment, in the first instance. Because the process of the present invention furnishes aqueous nutrient medium in the form of a mist, fog or spray, the extracellular release does not remain in the locality of the cultivar long enough to have as great an inhibitory effect upon growth as when released into the surrounding aqueous body of a natural habitat. Particularly where the water is delivered in relatively larger particle sizes, the extracellular products are rather effectively dispersed.

Three factors are known to control the distribution of oxygen in water. They are: (1) temperature and salinity, (2) biological activity, and (3) currents and mixing processes. In the natural habitat many hydrophytes may be subjected to periodic oxygen deficits if there is rigorous growth or associated biological activity taking place in the water. An important practical advantage of the process of the invention resides in the fact, that under atmospheric cultivation periodic oxygen deficits can be controlled easier because the rate of supply is not withheld by the delay of diffusion of the oxygen into the water. We believe it is easier to supply large volumes of plant biomass with oxygen via the atmosphere than by pumping air or oxygen into water. Moreover, under conventional underwater cultivation techniques in tanks and pools, a misjudgment about oxygen requirements can result in poisonous and unpleasant hydrogen sulphide fumes which are released into the atmosphere and water and which are both dangerous and extremely unpleasant to the cultivators.

Perhaps one of the most significant advantages of the invention is the ability to deliver nutrients or fertilizers to the plants on an economical basis. Thus, when plants are grown intensively as an aquacultural crop they typically will rapidly deplete the water of essential nutrients, especially nitrogen and phosphorus. In general, it is impracticable to deliver fertilizers to plants being grown in a natural environment. In part, this is because of the difficulty of maintaining the nutrient in the area of interest, which is virtually impossible if there is any appreciable current flow or wave action. Likewise, since the nutrient is dispersed in a large body of water, the amounts required to achieve effective results are excessive. Apart from the foregoing, it is difficult to maintain the fertilizer in solution or suspension in the aqueous medium long enough to be fully effective. All of these shortcomings are overcome in the process of the present invention, wherein plants, naturally occurring in aqueous media, are grown in the atmosphere and are supplied with nutrients by a fine mist or spray of the nutrient medium. Where nutrient additions are desired, they may be added to the basic water medium shortly before being sprayed on the plants, so that the nutrients are not only utilized in a timely manner, but they are efficiently directed to the plant. In addition, nutrients may be added in a controlled manner around applications of growth regulators, hormones, herbicides, growth substances and disease controlling agents.

Among the other significant advantages of the new process, in providing for the cultivation of aquatic and marine plants in a water charged atmospheric environment, are a high degree of control over the growth characteristics of the plant. For example, light intensity may be carefully controlled, so as to be screened during periods of excessive intensity and enhanced during periods of lower intensity, achieving not only a longer growth period than in the natural habitat, but providing for sustained optimal growth rates throughout the period of photosynthetic activity. Temperature may be effectively controlled by employing a water charged atmospheric environment to maintain a uniform level of temperature for optimum growth without quick changes about the uniform optimum. When necessary or desirable, artificial light may be provided and/or external heat, so that the normal growth season may be significantly extended in many instances.

It should be understood, of course, that the specific forms of the invention herein illustrated and described are intended to be representative only, as many changes may be made therein without departing from the clear teachings of the disclosure. Accordingly, reference should be made to the following appended claims in determining the full scope of the invention.

We claim:
1. The method of cultivating freshwater and marine macrophytes of the type naturally growing in water comprising the steps of:
   (a) providing a controlled atmospheric environment;
   (b) exposing said environment to light sufficient to support growth of said macrophytes;
   (c) placing live macrophytes in said environment in a position exposed to said light; and
   (d) wetting said macrophytes with water of the type in which they naturally grow to maintain only a film of water on said macrophytes substantially throughout their growth period.
2. The method according to claim 1 wherein:
   (a) the atmospheric environment is enclosed and exposed to direct sunlight.
3. The method according to claim 2 wherein:
   (a) the wetting of said macrophytes is effected by spraying said atmospheric environment with said water to produce a water charged atmosphere.
4. The method according to claim 3 wherein:
   (a) the atmospheric environment is charged with up to five orders of magnitude less water per cubic volume than normally present in the same volume of water in which the macrophytes naturally grow.
5. The method according to claim 3 wherein:
   (a) the water charged atmosphere is maintained at a relatively humidity of substantially 100%.
6. The method according to claim 3 wherein:
   (a) the spraying of water is effected by atomizing said water with air.

7. The method according to claim 3 wherein:
   (a) the spraying of water is effected by atomizing said water with air and at least periodically with air and $CO_2$.
8. The method according to claim 3 further comprising the step of:
   (a) controllably introducing nutrient additives into said water prior to said spraying operation.
9. The method according to claim 3 further comprising the step of:
   (a) maintaining the temperature of said environment within a substantially uniform range promoting optimum growth of said macrophytes.
10. The method according to claim 9 wherein:
    (a) the temperature of the environment is at least partially controlled by varying the particle size of the spray.
11. The method according to claim 3 wherein:
    (a) said enclosed environment is in a housing located on the ground; and
    (b) said water is obtained directly from a groundwell.
12. The method according to claim 11 wherein:
    (a) the macrophytes are those naturally growing in sea water; and
    (b) the water used in spraying the environment is sea water.
13. The method according to claim 3 further comprising the step of:
    (a) draining the live macrophytes of water in excess of said film.
14. The method according to claim 13 wherein:
    (a) the live macrophytes are placed in said environment to permit free circulation of water charged air in and about them to effect said draining.
15. The method according to claim 14 wherein:
    (a) the live macrophytes are loosely placed in said environment and tumbled to periodically expose all of them to said light.
16. The method of cultivating macroalgae propagates, which comprises:
    (a) providing a clean, grease-free core of a plastic material;
    (b) inserting the core within an expandable netting;
    (c) loosely packing mature, reproductive macroalgae within the space surrounding the core and bounded by the netting;
    (d) placing the packaged macroalgae in an environment conducive for growth to establish propagates of said macroalgae on said core; and
    (e) removing the adult plants and cultivating the remaining propagates in an environment conducive to growth.
17. Apparatus for cultivating freshwater and marine macrophytes of the type naturally growing in water comprising:
    (a) means providing a controlled atmospheric environment;
    (b) means for exposing said environment to light;
    (c) support means for supporting said macrophytes in said environment said support means being adapted to loosely support said macrophytes and being further adapted to permit light, air and water to pass therethrough;
    (d) wetting means for wetting said macrophytes with water of the type in which they naturally grow to maintain only a film of water on said macrophytes substantially throughout their growth period; and
    (e) tumbling means for tumbling said macrophytes in air to periodically expose all of them to said light.
18. The apparatus according to claim 17 wherein:
    (a) the wetting means includes a plurality of spray means located within said environment for spraying said environment with water to produce a water charged atmosphere.
19. The apparatus according to claim 18 further including:
    (a) means for maintaining said environment with up to five orders of magnitude less water per cubic volume than normally present in the same volume of water in which the macrophytes naturally grow.
20. The apparatus according to claim 18 wherein:
    (a) the spray means includes means for mixing water with air and $CO_2$ for atomizing said water and introducing it along with said $CO_2$ into the environment.
21. The apparatus according to claim 18 wherein:
    (a) the spray means includes control means for varying the size of the water particles introduced into said environment to at least partially control the temperature of the environment.
22. The apparatus according to claim 18 wherein:
    (a) said tumbling means includes spray means.
23. The apparatus according to claim 18 wherein:
    (a) said tumbling means is adapted to impart motion to said support means to tumble said macrophytes.
24. The apparatus according to claim 18 wherein:
    (a) said support means includes a plurality of cylindrically shaped rotary racks constructed of an open mesh for loosely supporting said macrophytes internally thereof and for permitting light, air and water to pass therethrough; and
    (b) means for horizontally supporting said racks for rotation about their longitudinal axes for tumbling the macrophytes to periodically expose all of them to said light.
25. The method of claim 16, further characterized by
    (a) said propagates being removed to a growth environment consisting of a protected, artificially or naturally lighted, moisture-charged atmosphere.

* * * * *

UNITED STATES PATENT AND TRADEMARK OFFICE
CERTIFICATE OF CORRECTION

PATENT NO. : 4,209,943

DATED : July 1, 1980

INVENTOR(S) : Henry W. Moeller and James P. Hunt

It is certified that error appears in the above-identified patent and that said Letters Patent are hereby corrected as shown below:

On the cover page, column 1, at [76] Inventors:
"Lyster Bay" should read --Oyster Bay--.

Signed and Sealed this

Sixteenth Day of December 1980

[SEAL]

Attest:

SIDNEY A. DIAMOND

Attesting Officer

Commissioner of Patents and Trademarks